United States Patent [19]

Kung

[11] Patent Number: 5,130,117
[45] Date of Patent: Jul. 14, 1992

[54] RADIOHALOGENATED BENZAZEPINE DERIVATIVES AND METHOD OF IMAGING DOPAMINE RECEPTORS THEREWITH

[75] Inventor: Hank F. Kung, Wynnewood, Pa.

[73] Assignee: Trustees of the University of Pennsylvania, Philadelphia, Pa.

[21] Appl. No.: 637,341

[22] Filed: Jan. 4, 1991

Related U.S. Application Data

[62] Division of Ser. No. 332,625, Apr. 3, 1989, Pat. No. 5,068,326.

[51] Int. Cl.$^5$ .................. A61K 49/02; C07D 223/16
[52] U.S. Cl. ..................................... 424/1.1; 540/594
[58] Field of Search .......................... 424/1.1; 540/594

[56] References Cited

PUBLICATIONS

O'Boyle, K. M., Waddington, T. L., Eur. J. Pharmacol., 1985, 115, 291.
Seeman, P., Niznik, H. B., Atlas of Science: Pharmacology 161, 1988.
Friedman, A. M., Dejesus, O. T., Woolverton, W. L. et al., Eur. J. Pharmacol., 1985, 108, 327.
Manik, C. P., Molinoff, P. B., McGonigle, P., J. Neurochemistry, vol. 51, No. 2, p. 391, 1988.
Kung, H. F., Billings, J., Guo, Y.-Z., Blau, M., Ackerhalt, R. A., Intl. J. Nucl. Med. Biol., 1988, 15, 187.
McQuade, R. D., Chipkin, R., Amaliky, N. et al., Life Sciences, vol. 43, pp. 1151-1160 (1988).
Farde, L., Halldin, C., Stone-Elander, S. et al., Psychopharmacol., 1987, 92, 278.
McQuard, R. D., Ford, D., Duffy, R. A., Chipkin, R. D., Iorio, L. C., and Barnett, A., Life Sciences, vol. 43, pp. 1861-1869 (1988).
Pfeiffer, F. R. et al., J. Med. Chem., vol. 25, No. 4, Apr. 1982, pp. 352-358.
Vandort, M. E. et al., J. Nucl. Med., vol. 28, No. 4, Apr. 1987, pp. 726-727, Abstract No. 719.
Kung, H. F. et al., Chemical Abstracts, vol. 108, No. 17, Apr. 1988, p. 367, Abstract No. 146340f and Nucl. Med. Biol., 1988, 15(2), 187-193.
Billings, J. et al., Chemical Abstracts, vol. 111, No. 19, Nov. 1989, p. 89, Abstract No. 167501m and Life Science, 1989, 45(8), 711-718.
Chumpradit, S. et al., J. Med. Chem., vol. 32, No. 7, Jul. 1989, pp. 1431-1435.
McQuade, R. D. et al., Chemical Abstracts, vol. 110, No. 9, Feb. 1989, p. 41, Abstract No. 69252r and Life Science, 1988, 43(23), 1861-1869.
Barnett, A. et al., Chemical Abstracts, vol. 110, No. 15, Apr. 1990, pp. 20-21, Abstract No. 128068k and Symp. Neurosci, 1988, 69-79.

Primary Examiner—John S. Maples
Attorney, Agent, or Firm—Woodcock Washburn Kurtz Mackiewicz & Norris

[57] ABSTRACT

Novel CNS dopamine D-1 receptors, such as the compound (±)-8-chloro-2,3,4,5-tetrahydro-3-methyl-5-(4'-[$^{125}$I]iodophenyl)-1H-3-benzazepine-7-ol, are disclosed. These compounds are useful as imaging agents for D-1 receptors in the human brain and exhibit good brain retention and in vivo stability.

2 Claims, 1 Drawing Sheet

RADIOHALOGENATED BENZAZEPINE DERIVATIVES AND METHOD OF IMAGING DOPAMINE RECEPTORS THEREWITH

This is a division of application Ser. No. 332,625, filed Apr. 3, 1989, now U.S. Pat. No. 5,068,326.

BACKGROUND OF THE INVENTION

This invention relates to benzazepine derivatives which are selective for dopamine D-1 receptors, to methods of preparing such compounds, to methods of utilizing them as imaging agents, and to novel compounds useful as intermediates in the preparation of such D-1 receptors.

For the treatment of a wide variety of different nervous and mental diseases, it is desirable to be able to monitor the effectiveness of drugs and substances which affect brain chemistry. For instance, in the treatment of schizophrenia or Parkinson's Disease, it is highly desirable to be able to gauge the biochemical effects of drugs administered for blocking the patient's dopamine receptors. If too little of the drug is administered, the desired blockade does not occur, and if too much of the drug is administered, there can be severe side effects.

New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs is based upon the comparisons made.

It is generally accepted that there are two subtypes of dopamine receptors, designated as D-1 and D-2 receptors. Recent reports have suggested that these two subtypes of receptors exhibit opposite biochemical effects: D-1 agonists stimulate adenyl cyclase activity, while D-2 agonists inhibit the enzyme activity. It is clear that these receptor subtypes influence each other, and yet they display separate and distinct functions on body physiology and biochemistry. Monitoring of D-1 receptors in a patient is important for assessing the dopaminergic system and ultimately assisting patient management.

The compound R-(+)-8-chloro-2,3,4,5-tetrahydro-3-methyl5-phenyl-1H-3-benzazepine-7-ol (SCH-23390) is a highly selective central D-1 antagonist. O'Boyle, K. M., Waddington, T. L., *Eur. J. Pharmacol.*, 1985, 115, 291; Seeman, P., Niznik, H. B., Atlas of Science: Pharmacology 161, 1988. The corresponding bromo- and iodo- compounds (SKF-83566 and IBZP, respectively) have also been shown to have a high specificity for central D-1 dopamine receptors. Friedman, A. M., Dejesus, O. T., Woolverton, W. L., et al., *Eur. J. Pharmacol.*, 1985, 108, 327; Manik, C. P., Molinoff, P. B., McGonigle, P., *J. Neurochemistry*, Vol. 51, No. 2, p. 391, 1988; Kung, H. F., Billings, J., Guo, Y.-Z., Blau, M., Ackerhalt, R. A., *Intl. J. Nucl. Med. Biol.*, 1988, 15, 187; McQuade, R. D., Chipkin, R., Amlaiky, N. et al., *Life Sciences*, Vol. 43, pp. 1151–1160 (1988). The in vitro affinity constants for these compounds in the rat striatum tissue preparation are set forth in Table 1.

TABLE 1

Chemical Structures and In Vitro Binding Constants of Benzazepines

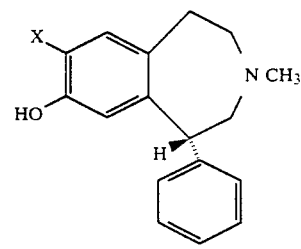

| Compound | X | Kd(nM) |
|---|---|---|
| SKF-83692 | H | 197 |
| SCH-23390 | Cl | 0.36 |
| SKF-83566 | Br | 2.32 |
| IBZP | I | 0.7 |

The bromo compound SKF-83566 labeled with [86]Br, a positron emitting radionuclide, has been used for PET (positron emission tomography) imaging in a rhesus monkey, which showed the highest concentration in the basal ganglia, with more selectivity in the posterior aspect of the caudate nucleus, the region with high D-1 receptor density. Friedman, A. M., Dejesus, O. T., Woolverton, W. L., supra. Several recent reports have indicated that in conjunction with PET, [$^{11}$C]SCH-23390 showed the highest concentration in the basal ganglia area of the human brain. Farde, L., Halldin, C., Stone-Elander, S., et al., *Psychopharmacol.*, 1987, 92, 278; McQuade, R. D., Ford, D., Duffy, R. A., Chipkin, R. D., Iorio, L. C. and Barnett, A., *Life Sciences*, Vol. 43, pp. 1861–1869 (1988).

The potential of a radioiodinated benzazepine derivative, [$^{125}$I]BZP as a specific CNS D-1 dopamine receptor imaging agent for SPECT has been reported. Kung, H. F., Billings, J., Guo, Y.-Z., Blau, M., Ackerhalt, R. A., Id. The agent exhibited good localization in rat brains after an intravenous injection, with an uptake of 2.7, 1.2, 0.8 and 0.26 %dose/organ at 2, 15, 30 and 60 minutes post injection, respectively. The regional distribution of [$^{125}$I]BZP in rat brain, as measured by in vivo autoradiography, displayed a high uptake in the caudate putamen, accumbens nucleus and substantia nigra, regions known to have a high concentration of D-1 dopamine receptors. The uptake ratio of striatum/cerebellum increased with time. At thirty seconds and two hours after injection, the ratios were 1.1 and 5.3, respectively. The specific uptake regions (as measured by in vivo autoradiography), rich in D-1 dopamine receptors, can be blocked by pretreatment with SCH-23390, a selective D-1 dopamine receptor antagonist.

IBZP suffers two major disadvantages as a potential imaging agent. The first disadvantage is the poor in vivo and in vitro stability of the compound based on observations of the in vivo biodistribution study of [$^{125}$I] IBZP in rats. The thyroid uptake is high at later time points, which strongly suggests the availability of free iodide in the blood circulation due to in vivo deiodination. Deiodination may take place because the radioactive iodine is at an activated position, ortho to the hydroxyl group on the benzene ring. The second drawback of [125I-]IBZP is its short retention time in the brain. In a normal SPECT study of the brain, it takes about thirty to sixty minutes for the data acquisition. It is necessary to use an agent exhibiting a prolonged retention time in the target region (in this case, basal ganglia) for SPECT imaging studies.

Although the compound SCH-23390 is a highly selective D-1 antagonist, its use as an imaging agent is diminished by the absence of a diagnostically suitable radioisotope such as 123I.

There is, therefore, a need for improved CNS D-1 dopamine receptor imaging agents which overcome the disadvantages of the various imaging agents known in the art.

SUMMARY OF THE INVENTION

Test results indicate that the novel compounds of Formula I are highly selective for the CNS D-1 receptor and should therefore possess utility as imaging agents for evaluation of such receptors.

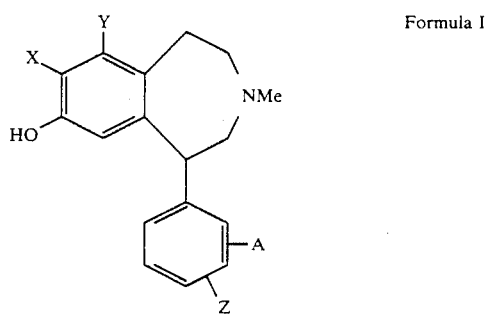

Formula I where
X = OH, Cl or $CH_3$;
Y = H, Cl, or $CH_3$, provided that, when X = Cl, then Y = H or $CH_3$ and when Y = H or $CH_3$, then X = Cl;
Z = Hal (halogen); C=CH-Hal; $C_1$–$C_{10}$ alkylene-Hal; $C_1$–$C_{10}$ alkylene-C=CH-Hal; $C_1$–$C_{10}$ alkylene-phenyl-Hal; or $C_1$–$C_{10}$ alkylene-heteroaryl-Hal; and
A = H, $C_1$–$C_5$ alkyl, $C_1$–$C_5$ alkylene-phenyl; or $C_1$–$C_5$ alkylene-heteroaryl.

This invention therefore relates to the novel compounds of Formula I, to methods of preparing them and to methods of utilizing them as imaging agents for the evaluation of CNS D-1 receptors. This invention further relates to novel compounds of Formula II which are useful as intermediates for preparing the novel compounds of Formula I.

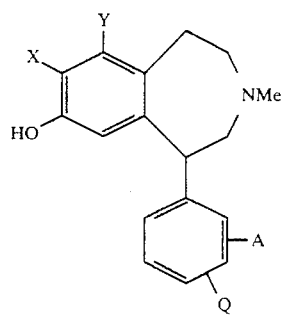

Formula II where Q = Hal, $SnBu_3$, $Si(R)_3$ or HgR;
X, Y and A are as defined above, and
R = $C_1$–$C_5$ alkyl.

DETAILED DESCRIPTION OF THE INVENTION

Figure 1:
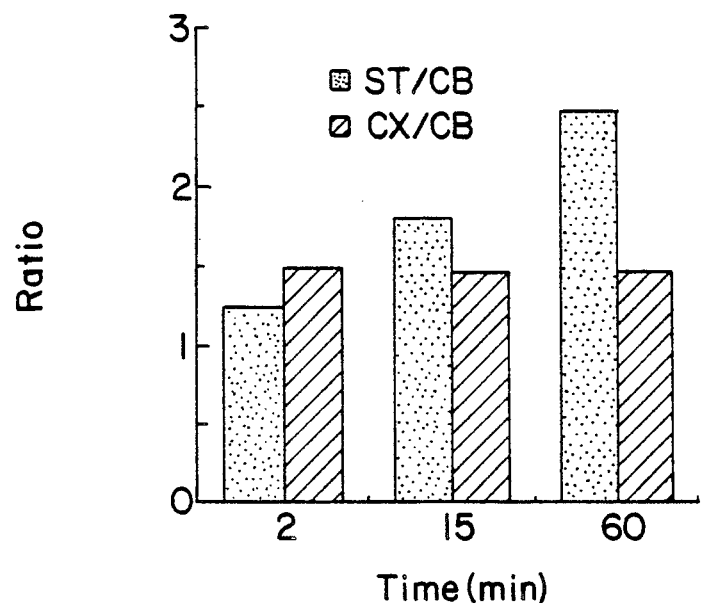
FIG. 1 is a bar graph showing ratios (based on % dose/gram) of regional cerebral uptake of [125I]FISCH (CX: cortex, ST: striatum, CB: cerebellum). Only ST/CB ratio shows the dramatic increase with time, suggesting that the agent is concentrated in the target tissue, in which the concentration of D-1 dopamine receptors is high.

Compounds of this invention may be made by methods analogous to that illustrated in Scheme A for the preferred compound of this invention, (±)-8-chloro-2,3,4,5-tetrahydro-3-methyl-5-(4'-[125I]iodophenyl)-1H-3-benzazepine-7-ol, referred to hereinafter as FISCH.

SCHEME A

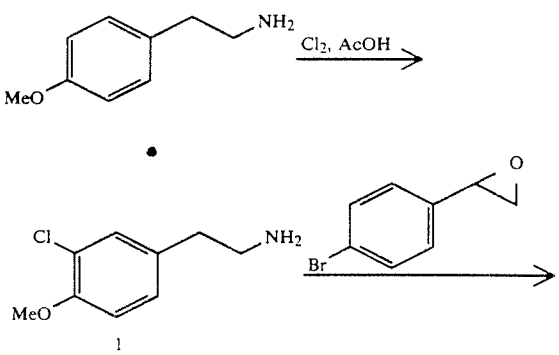

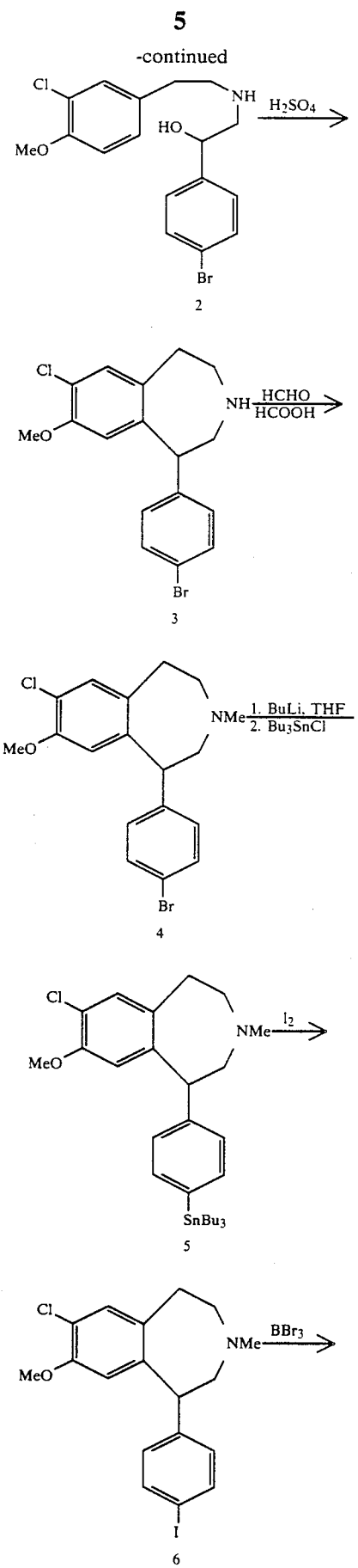
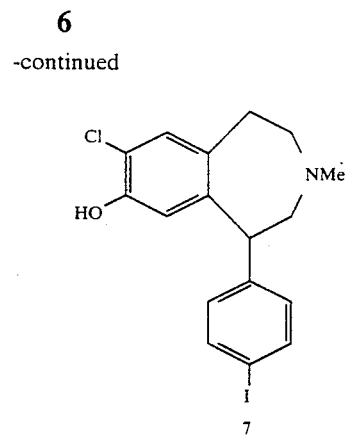
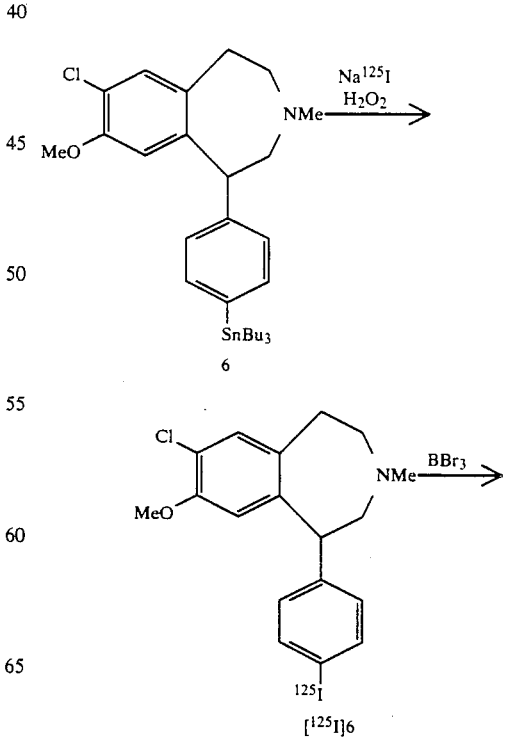

As shown in Scheme A, the 4'bromo-benzazepine, 3, may be prepared from 3-chloro-4-methoxyphenethyl amine, 1, using methods disclosed by Wyrick, S. C., Mailman, R. B., *J. Label. Compd. and Radiopharm.*, 1984, 22, 189, the disclosure of which is hereby incorporated by reference. The 4'bromo-benzazepine, 4, may be prepared by N-methylation of 3 with formaldehyde and formic acid. Lithiation of 4 with n-butyllithium at −78 C., to replace the 4'-bromo group, followed by the addition of tri-n-butyltin chloride, affords the desired tri-n-butyltin derivative, 5. The final product, 7, may be prepared by contacting 5 with iodine ($I_2$) and then deprotecting the hydroxy group with a suitable deprotecting agent such as boron tribromide or a strong acid to give the final product, 7, FISCH. Although Scheme A illustrates the use of the tributyltin intermediate 5, other intermediates within the scope of Formula II could also be utilized.

Radiolabeled compounds of the invention ma be prepared by methods analogous to those illustrated in Scheme B for radiolabelling of FISCH.

SCHEME B

-continued

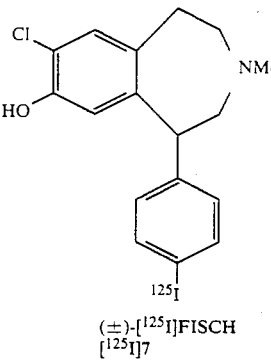

(±)-[125I]FISCH
[125I]7

Intermediate compound 5 is labeled with, for example, I-125 at carrier-free level by an electrophilic radioiodination reaction using an oxidant such as hydrogen peroxide. The radiolabeled compound, 6, is separated from the starting material, 5, by HPLC. The carrier-free [125I] 6 is O-demethylated by boron tribromide and the desired final product [125I]FISCH, 7, is separated again from the impurity by HPLC. Although 125I-isotopes are useful for laboratory testing, they will generally not be useful for actual diagnostic purposes because of the relatively long half-life (60 days) and low gamma-emission (30-65 Kev) of 125I. The isotope 123I has a half life of 13 hours, gamma energy 159 keV), and it is therefore expected that labeling of ligands to be used for diagnostic purposes would be with this isotope. Other isotopes which may be used include 121I (half life of 2 hours).

Evaluations of FISCH indicate that it shows good brain uptake in rats. The high initial uptake (2.27% dose/organ) at two minutes after injection indicates that the compound passes through the blood-brain barrier with ease.

The maximum brain uptake for rats, i.e. 100% first pass extraction, is between 2.5-4.0% of the injected dose. Kung, H. F. in Fritzberg, A., ed., *Advances in Radiopharmaceuticals*, CRC Press, Boca Raton, Fla., 1986, Vol. 1, pp. 21-40. At later time points, brain uptake decreases; at one hour after injection of all of the [125I]FISCH, activity had washed out from the brain (0.55% dose/organ). The brain retention at one hour post injection was much better than that of [125I]IBZP (0.26% dose/organ).

High initial uptake of FISCH in the lungs was also observed with rapid clearance at fifteen and sixty minutes. Liver uptake remains high throughout the first hour. The relatively low thyroid uptake at one hour post injection (0.04%) suggests that little in vivo deiodination of [125I]FISCH has occurred. As compared with [125I]IBZP, which showed a thyroid uptake of 0.1% at one hour post injection, the new iodinated D-1 agent of this invention, [125I]FISCH, containing an iodine atom at the 4'-position, displays better in vivo stability.

Utilizing a brain regional dissection technique, the stratum/cerebellum (ST/CB) ratio (target to nontarget ratio) for FISCH displayed a dramatic increase with time: 1.24, 1.80 and 2.47 at two, fifteen and sixty minutes, respectively. These data are consistent with the distribution pattern obtained with in vivo autoradiography.

Figure 2:
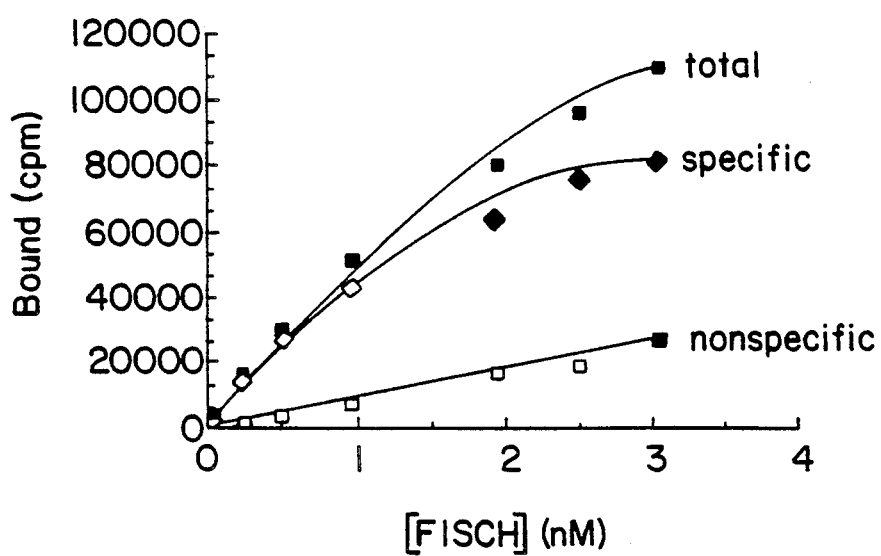
FIG. 2 is a graph showing the saturation binding curve of [125I]FISCH in rat striatum. The radiolabeled [125I]FISCH binds to rat striatal homogenate with high affinity. The saturation curve indicates that this ligand demonstrates a low nonspecific binding (approximately 15% at Kd).

Tests to determine in vitro bonding of [125I]FISCH and [125I]TISCH (the 3'-iodo analog of FISCH) indicate that the compounds bind with high affinity to rat striatal homogenate. The saturation curve shown in FIG. 2 indicates that this ligand has a fairly low nonspecific binding (approximately 15% at Kd). The specific binding of [125I]FISCH and [125I]TISCH (racemic mixture) was found to be saturable and displayed a Kd of 1.43 and 0.35 nM, respectively. These values were comparable to those for [125I]IBZP (R-(+), active form), measured under similar conditions. Competition data of various compounds for [1125I]FISCH and TISCH binding are presented in Tables 2 and 3. The results indicate that [125I]FISCH and TISCH bind specifically to the dopamine D-1 receptor with high selectivity.

TABLE 2

Inhibition Constants of Compounds on [125I]FISCH Binding to Rat Striatal Membranes*

| Compound | ki (nM, mean + SEM) |
|---|---|
| (±) FISCH | 1.71 ± 0.17 |
| SCH-23390 | 0.39 ± 0.04 |
| (±) IBZP | 13.40 ± 0.54 |
| (−)-Apomorphine | 888 ± 115 |
| WB 4101** | 1270 ± 203 |
| ketanserin | >3000 |
| spiperone | >3000 |

*0.15-0.30 nM [125I]FISCH was incubated in the presence of the indicated compounds in 7-11 concentrations and of membrane preparation from rat striatum. Each value represents the mean ± SEM of three to five determinations.
**WB4101 is the compound 2-(2,6-dimethoxyphenoxyethyl)-aminomethyl-1,4-benzodioxane hydrochloride

TABLE 3

Inhibition Constants of Compounds on [125I]TISCH Binding to Rat Striatal Membranes*

| Compound | ki (nM, mean + SEM) |
|---|---|
| (R)-SCH-23390 | 0.41 ± 0.04 |
| (±)-TISCH | 0.55 ± 0.05 |
| (±)-FISCH | 2.07 ± 0.35 |
| (±)-Br-TISCH | 2.84 ± 0.21 |
| Spiperone | 488 ± 58 |
| Ketanserin | 1881 ± 225 |
| Apomorphine | >2000 |
| Propanolol | >3000 |

The compounds of this invention can exist as either R- or S- isomers. It is important to note that the aforementioned data were obtained using a racemic mixture of FISCH. Optical resolution of the isomers has indicated that the R+ isomer is the active isomer and that the S- isomer is inactive.

The above-described test results indicate that [125I]-FISCH displays in vivo and in vitro properties superior to those of [125I]IBZP and suggest that the compound and the structurally related compounds encompassed by Formula I, especially in the form of the resolved active R-(+)-isomer, should when appropriately labeled be useful imaging agents for imaging D-1 receptors in the living human brain using well-known methods such as SPECT. By virtue of their D-1 receptor capability, the novel compounds of Formula I may also possess as yet undefined therapeutic value.

Preferred compounds of this invention are those wherein, independently or in combination, (1) Y=H and X=Cl; (2) A=H; (3) Hal=I; (4) Hal=$^{123}$I, $^{125}$I or $^{131}$I; and (5) Z=Hal. Specific examples of compounds contemplated within the scope of this invention ar presented in Table 3.

TABLE 3

| X | Y | Z | A |
|---|---|---|---|
| Cl | H | 4'-Br | H |
| Cl | H | 4'-Cl | H |
| OH | Cl | 4'-I | H |
| Cl | H | 4'-CH=CHI | H |
| Cl | H | 4'-CH$_2$I | H |
| Cl | H | 4'-CH$_2$CH$_2$I | H |
| Cl | H | 4'-CH$_2$—PhI | H |
| Cl | H | 4'-CH$_2$—I | H |
| Cl | H | 4'-(CH$_2$)$_2$CH=CHI | H |
| Cl | H | 3'-CH=CHI | H |
| Cl | H | 3'-CH$_2$I | H |
| Cl | H | 3'-CH$_2$CH$_2$I | H |
| Cl | H | 3'-CH$_2$—PhI | H |
| Cl | H | 3'-CH$_2$—I | H |
| Cl | H | 3'-(CH$_2$)$_2$CH=CHI | H |
| Cl | H | 3'-I | H |
| Cl | H | 5'-I | H |
| Cl | H | 2'-I | H |
| Cl | H | 6'-I | H |
| Cl | H | 4'-I | 2'-CH$_3$ |
| Cl | H | 4'-I | 2'-CH$_3$Ph |
| CH$_3$ | H | 4'-Br | H |
| CH$_3$ | H | 4'-Cl | H |
| CH$_3$ | Cl | 4'-I | H |
| CH$_3$ | H | 4'-CH=CHI | H |
| CH$_3$ | H | 4'-CH$_2$I | H |
| CH$_3$ | H | 4'-CH$_2$CH$_2$I | H |
| CH$_3$ | H | 4'-CH$_2$—PhI | H |
| CH$_3$ | H | 4'-CH$_2$—I | H |
| CH$_3$ | H | 4'-(CH$_2$)$_2$CH=CHI | H |
| CH$_3$ | H | 3'-CH=CHI | H |
| CH$_3$ | H | 3'-CH$_2$I | H |
| CH$_3$ | H | 3'-CH$_2$CH$_2$I | H |
| CH$_3$ | H | 3'-CH$_2$—PhI | H |
| CH$_3$ | H | 3'-CH$_2$—I | H |
| CH$_3$ | H | 3'-(CH$_2$)$_2$CH=CHI | H |
| CH$_3$ | H | 3'-I | H |
| CH$_3$ | H | 5'-I | H |
| CH$_3$ | H | 2'-I | H |
| CH | H | 6'-I | H |
| CH$_3$ | H | 4'-I | 2'-CH$_3$ |
| CH$_3$ | H | 4'-I | 2'-CH$_3$Ph |

The preparation and testing of the compounds of this invention are discussed in more detail in the following examples which are not intended to limit the scope of this invention. In all examples, Proton NMR was recorded on a Varian EM 360A spectrometer. The chemical shifts were reported in ppm downfield from an internal tetramethylsaline standard. Infrared spectra were obtained with a Mattson Polaris FT-IR spectrometer. Melting points were determined on a Meltemp apparatus are reported uncorrected. Elemental analyses were performed by Atlantic Microlabs, Inc., of Norcross, Ga. and were within 0.4% of the theoretical values.

EXAMPLE 1

3-Chloro-4-methoxyphenethyl amine (1). Methoxyphenethyl amine (39.4 g, 0.261 mol) was dissolved in water (300 mL) and concentrated HCl(22mL). To this solution was added chlorine gas (20.3 g, 0.287 mol) in glacial acetic acid (300 mL) over a 15 minute period while maintaining the temperature below 35° C. After standing for ten minutes, the volatiles were removed in vacuo and the dark solid residue was dissolved in absolute ethanol (100 mL) and allowed to crystallize at −10° C. The collected precipitate was dissolved in a mixture of saturated sodium bicarbonate (400 mL) and dichloromethane (400 mL). The organic layer was separated and dried over anhydrous sodium sulfate. It was condensed on a rotorevaporator to afford a dark oil which was distilled (115°-116° C./1.75 mm Hg) to give 12.8 g(26.4%) of a clear oil. IR (neat) 3600–3310 (br,NH$_2$), 1600, 1500, 1250 and 1060 cm$^{-1}$; 1H NMR(CDCl$_3$)δ,d 7.36-6.71 (m, 3H, ArH), 3.85 (S, 3H, OCH$_3$), 3.15–2.48 (m, 4H, (CH$_2$)$_2$), 1.12(S, 2H, NH$_2$).

EXAMPLE 2

N-[2-(4'-Bromophenyl)-2-hydroxyethyl]-3-chloro-4-methoxyphenethylamine (2). Compound 2 (6.40 g, 0.034 mol) and 4-bromostyrene oxide (6.90 g, 0.034 mol) were dissolved in acetonitrile (50 mL) and refluxed overnight. The solvent was evaporated under reduced pressure and a gummy residue was triturated with ether. The white powder was filtered to afford 6.5 g (40%): mp 83°-84° C., IR (KBr)λ3400 (br, NH), 3140 (br, OH), 1500, 1400, 1250, 1050 cm$^{-1}$; 1H NMR (CDCl$_3$)δ,d 7.60-6.70 (m, 7H, ArH), 4.80-4.48 (m, 1H, CH), 3.85 (S, 3H, OCH$_3$), 3.00–2.40 (m, 6H, (CH$_2$)$_3$), 2.55 (S, 1H, NH).

EXAMPLE 3

7-Chloro-8-methoxy-1-(4,-bromophenyl)-2,3,4,5-tetrahydro-1H-3-benzazepine (3). The hydroxy amine, 3 (7.4 g, 0.019 mol), was added in portions to concentrated sulfuric acid (60 mL) with stirring, keeping the temperature below 12° C. The reaction mixture was then stirred at 8° C. for 30 min. and then at room temperature for 90 min. The mixture was poured into ice (500 g); concentrated ammonium hydroxide (100 mL) was added followed by solid sodium hydroxide (40 g) while maintaining the temperature below 30° C. The precipitate was extracted into dichloromethane and the organic layer was dried over anhydrous sodium sulfate and evaporated under reduced pressure to afford 6.5 g (93%) of a light yellow solid, which was purified by column chromatography (silica gel, CH$_2$Cl$_2$:MeOH:N-H$_4$OH;95:5:l) to obtain 3, 5.9 g (84%): mp 139°-140° C. (lit 136°-37° C.);FT-IR(KBr)δ3430 (br,NH), 1500, 1480, 1400, 1050 cm$^{-1}$; 1H NMR (CDCl$_3$)δ,d 7.65-7.31 and 7.10–6.89 (AA'BB', 4H, ArH'), 7.13 (S, 1H, ArH #6), 6.50 (S, 1H, ArH #9) 4.29–4.05 (m, 1H, CH), 3.72 (S, 3H, OCH$_3$), 3.45–2.53 (m, 6H, (CH$_2$)$_3$), 1.92 (S, 1H, NH).

EXAMPLE 4

7-Chloro-8-methoxy-1-(4'-bromophenyl)-3-methyl-2,3,4,5-tetrahydro-1H-3-benzazepine (4). To a solution of benzazepine 3 (7.20 g, 19.6 mmol) in formic acid (2.3 g) was added 37% benzaldehyde (1.8 g). The mixture was heated to 90°-100° C. for four hours. After cooling the reaction mixture to room temperature, 4N hydrochloric acid solution (5.16 mL) was added. The mixture was condensed to dryness under reduced pressure. The residue was dissolved in water and then made basic with 25% sodium hydroxide solution. The mixture was extracted three times with dichloromethane. The combined organic layers were dried over anhydrous sodium sulfate. The solvent was evaporated to obtain a solid which was purified by column chromatography (silica gel; $CH_2Cl_2$:MeOH:$NH_4OH$;95:5:1) to give 4, 6.0 g (80%) mp 116°-118° C.; FT-IR (KBr)$\lambda$1500, 1380, 1270 and 1060 cm$^{-1}$; $^1$H NMR (CDCl$_3$)$\delta$,d 7.65-7.35 and 7.21-6.90 (AA'BB',4H, ArH'), 7.13 (S, 1H, ArH #6), 6.38 (S, 1H, ArH #9), 4.40-4.10 (m, 1H, CH), 3.70 (S, 3H, OCH$_3$), 3.10-2.45 (m, 6H, (CH$_2$)$_3$), 2.37 (S, 3H, NCH$_3$). Anal. Calcd for $C_{18}H_{19}BrClNO$: C,H,N.

EXAMPLE 5

7-Chloro-8-methoxy-1-(4'-tri-n-butyltinphenyl)-3-methyl-2,3,4,5-tetrahydro-1H-3-benzazepine (5). The n-methyl benzazepine 4 (2.0 g, 5.2 mmol) in dried THF (50 mL) was cooled to −78° C. in a dry ice-acetone bath. To this solution, n-butyllithium (4.0 mL, 6.4 mmol) was added with stirring. The reaction solution turned dark red immediately. Tri-n-butyltin chloride (1.5 mL) was added to the reddish solution. After stirring at −78° C. for five minutes the reaction mixture was quenched with ammonium chloride solution (3 mL, saturated). The mixture was allowed to warm to room temperature and THF was evaporated under reduced pressure. The residue was extracted with dichloromethane. The organic layer was dried over anhydrous sodium sulfate. After evaporating the solvent, the desired product, 5, was separated by column chromatography (silica gel; $CH_2Cl_2$:MeOH:$NH_4OH$;95:5:1) to obtain 1.8 g (58%): FT-IR (neat)$\lambda$, 2960-2800 (strong and broad band of n-butyl group), 1600, 1500, 1405, 1270 and 1100 cm$^{-1}$; $^1$H NMR (CDCl$_3$)$\delta$, d 7.65-7.38 and 7.25-7.03 (AA'BB',4H, ArH'), 7.13 (S, 1H, ArH #6), 6.30 (S, 1H, ArH #9), 4.54-4.17 (m, 1H, CH), 3.60 (S, 3H, OCH$_3$), 3.10-2.59 (m, 6H, (CH$_2$)$_3$);2.40 (S, 3H, NCH$_3$), 1.70-0.65 (m, 27H, Sn(C$_4$H$_9$)$_3$). Anal. calcd. for $C_{30}H_{46}ClNOSn$: C,H,N.

EXAMPLE 6

7-Chloro-8-methoxy-1-(4'-iodophenyl)-3-methyl-2,3,4,5-tetrahydro-1H-3-benzazepine (6). A 0.1M solution of iodine in chloroform was added to a solution of tri-n-butyltin derivative of benzazepine 5 (500 mg, 0.85 mmol) in chloroform at room temperature until the color of iodine persisted. The mixture was stirred overnight at room temperature. Then a solution of potassium fluoride (1M, 1 mL, 1 mmol) in methanol and a 5% aqueous sodium bisulfite solution (1 mL) were added respectively. After five minutes of stirring, water (2 mL) was added. The organic layer was separated and the aqueous layer was extracted with chloroform twice. The combined organic layers were dried over anhydrous sodium sulfate. The solvent was evaporated under reduced pressure to obtain a yellow solid which was purified by column chromatography (silica gel; $CH_2Cl_2$:MeOH: $NH_4OH$; 95:5:1) to yield the product, 6: 342 mg (94%):mp 130°-132° C;. FT-IR (KBr)$\lambda$1500, 1460, 1400, 1260 and 1110 cm$^{-1}$; $^1$H NMR (CDCl$_3$)$\delta$,d 7.85-7.48 and 7.10-6.75 (AA'BB', 4H, ArH'), 7.13 (S,1H, ArH #6), 6.35 (S, 1H, ArH #9), 4.41-4.01 (m,1H, CH), 3.70 (S, 3H, OCH$_3$), 3.15-2.50 (m, 6H, (CH$_2$)$_3$), 2.38 (S, 3H, NCH$_3$). Anal. calcd. for $C_{18}H_{19}ClINO$: C, H, N.

EXAMPLE 7

7-Chloro-8-hydroxy-1-(4,-iodophenyl)-3-methyl-2,3,4,5-tetrahydro-1H-3-benzazepine (7). A solution of iodobenzazepine 6 (342 mg, 0.80 mmol), in dried dichloromethane, was cooled in a dry ice-isopropanol bath. To this stirred solution was added BBr$_3$ solution (1.6 mL, 1.6 mmol), dropwise. The reaction mixture was then allowed to warm to room temperature. The stirring was continued for two hours. The reaction mixture was partly concentrated and chilled in an ice bath. Methanol was added to the mixture and it was stirred for several hours at room temperature. After the methanol had been evaporated under reduced pressure, the residue was stirred with water. The mixture was made strongly basic with 10% sodium hydrozide. The precipitate was filtered. The pH of the filtrate was adjusted to 7-8 with dilute hydrochloric acid. The cloudy mixture was extracted several times with ethyl acetate. The combined organic layers were dried over anhydrous sodium sulfate. The solvent was evaporated under reduced pressure to obtain 110 mg (33%): mp 216°-218° C.; FT-IR (KBr)$\lambda$3450 (br, OH), 1500, 1460, 1400, 1100, 1060 and 1000 cm$^{-1}$; $^1$H NMR (CDCl$_3$+DMSO(d$_6$))$\delta$,d 7.80-7.52 and 7.10-6.85 (AA'BB', 4H, ArH'), 7.10 (S, 1H, ArH #6), 6.32 (S,1H, ArH,#9), 4.31-3.92 1H, (m, 1H, CH), 3.10-2.65 (m, 6H, (CH$_2$)$_3$), 2.35 (S, 3H, NCH$_3$). Anal. calcd. for $C_{17}H_{17}ClINO$: C, H, N.

EXAMPLE 8

Radiolabeling

Aqueous hydrogen peroxide (10 uL, 30% w/v) was added to a mixture of 10 $\mu$L of compound 5 (1 mg/mL), 100 $\mu$L of 50% EtOH/H$_2$O, 10 $\mu$L 1N HCl and 5 $\mu$L of sodium [$^{125}$I]iodide (2-3 mCi, carrier-free, Sp. Act. 2,200 Ci/mmol) in a sealed vial. The reaction was allowed to proceed at 23° C. for 2 hr, after which it was terminated by the addition of 0.5 ml of sodium bisulfite (100 mg/mL). The reaction mixture was made basic via the addition of 100 mg NaHCO$_3$ and extracted with ethyl acetate (3×1 mL). The combined organic layers were passed through an anhydrous sodium sulfate column (0.2 cm×5 cm), and evaporated to dryness by a stream of nitrogen. The residue was dissolved in 100% ethanol (50-100 $\mu$L), and the desired product, [$^{125}$I]6, was isolated from the unreacted compound 5 and a small amount of unknown radioactive impurities by HPLC using a reverse phase column (PRP-1, Hamilton Inc.) and an isocriatic solvent of 90% acetonitrile/10% pH 7.0 buffer (5 mM, 3,3-dimethyl glutaric acid). The appropriate fractions were collected, condensed, and re-extracted with ethyl acetate (1×3 ml). The solution containing the no-carrier added product was condensed to dryness and redissolved into 100% ethanol (purity 99%, overall yield 75%).

To an anhydrous $CH_2Cl_2$ solution of [$^{125}$I]6 under an argon atmosphere was added BBr$_3$ (40 $\mu$L, 1 M in $CH_2Cl_2$). The reaction was terminated after 1 hr at 23° C. The mixture was condensed to dryness, and the residue was dissolved into 100% EtOH (100 $\mu$L). The desired product, [$^{125}$I] FISCH, was again separated from a small amount of unknown radioactive impurities by the same HPLC system but using 80%/20% acetonitrile/buffer. The appropriate fractions were collected, condensed, and re-extracted with ethyl acetate (1×3 ml). The solution containing the no-carrier added product was condensed to dryness and redissolved into 100% ethanol (purity 99%, overall yield 75%). After dilution with saline, this agent was used in the in vivo and in vitro studies.

The following techniques were used in the in vivo and in vitro studies reported herein.

Biodistribution in Rats

Biodistribution of [$^{125}$I]FISCH was studied in male Sprague Dawley rats (225–300g) which were allowed free access to food and water. While under halothane anesthesia, 0.2 ml of a saline solution containing [$^{125}$I]FISCH was injected directly into the femoral vein, and the rats were sacrificed at various time points post injection by cardiac excision under halothane anesthesia. The organs of interest were removed, weighed and radioactivity was counted using a Beckman gamma automatic counter (Model 4000). The percent dose per organ was calculated by a comparison of the tissue counts to suitably diluted aliquots of the injected material. Total activities of blood and muscle were calculated assuming that they are 7% and 40% of total body weight, respectively.

Regional brain distribution in rats was obtained after an iv injection of [$^{125}$I]FISCH. By dissecting, weighing and counting samples from different brain regions (cortex, striatum, hippocampus and cerebellum), % dose/-gram of samples was calculated by comparing the sample counts with the counts of the diluted initial dose. The uptake ratio of each region was obtained by dividing % dose/gram of each region with that of the cerebellum.

Tissue Preparation

Male Sprague-Dawley rats (200–250g) were decapitated, and the brains were removed and placed in ice. Striatal tissues were excised, pooled and homogenized in 100 volumes(w/v) of ice-cold Tris-HCl buffer (50 mM), pH 7.4. The homogenates were centrifuged at 20,000×g for 20 min. The resultant pellets were rehomogenized in the same buffer and centrifuged again. The final pellets were resuspended in assay buffer containing: 50 mM Tris buffer pH 7.4, 120 mM NaCl, 5 mM KCl, 2mM CaCl$_2$ and 1 mM MgCl$_2$.

Binding Assays

The binding assays were performed by incubating 50 μl of tissue preparations containing 40–60μg of protein with appropriate amounts of [$^{125}$I]FISCH ligand and competitors in a total volume of 0.2 ml of the assay buffer. After an incubation period of 20 min at 37° C. (with stirring), the samples were rapidly filtered in the cell harvester (Brandel M-24R) under vacuum through Whatman GF/B glass fiber filters pretreated with 0.2% protamine sulfate and washed with 3×5ml of cold (4° C.) 50 mM Tris-HCl buffer, pH 7.4. The nonspecific binding was obtained in the presence of 10 μM SCH-23390. The filters were counted in a gamma counter (Beckman 5500) at an efficiency of 70%.

Data Analysis

Both Scatchard and competition experiments were analyzed using the iterative non-linear least squares curve-fitting program LIGAND.

What is claimed is:

1. A dopamine receptor agent comprising a compound of the formula

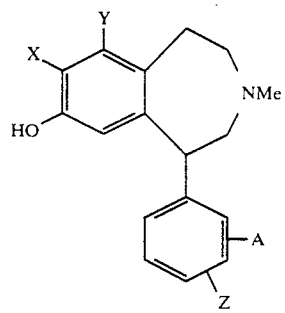

where
X is selected from the group consisting of OH, Cl and CH$_3$;
Y is selected from the group consisting of H, Cl and CH$_3$, provided that, when X is Cl, then Y is either H or CH$_3$, and when Y is H or CH$_3$, then X is Cl;
Z is selected from the group consisting of Hal; C═CH—Hal, alkylene—Hal; and C$_1$-C$_{10}$ alkylene—C═CH═Hal; C$_1$-C$_{10}$ alkylene-phenyl-Hal;
Hal is a radioactive halogen isotope; and
A is selected from the group consisting of H, C$_1$-C$_5$ alkyl, and C$_1$-C$_5$ alkylene-phenyl.

2. A method of imaging dopamine D-1 receptors in a patient comprising administering to said patient an effective quantity of the dopamine receptor imaging agent of claim 1 and measuring the gamma ray or photon emissions therefrom.

* * * * *

UNITED STATES PATENT AND TRADEMARK OFFICE
CERTIFICATE OF CORRECTION

PATENT NO. : 5,130,117

DATED : July 14, 1992

INVENTOR(S) : Hank F. Kung

It is certified that error appears in the above-identified patent and that said Letters Patent is hereby corrected as shown below:

Title page, item [56], under "References Cited"
--Amlaiky--.

Column 1, Line 58 delete "methyl5" and insert therefor --methyl-5--.

Column 3, Line 55 delete "$C_1 C_{10}$" and insert therefor --$C_1-C_{10}$--.

Column 9, line 9, please delete "Table 3" and insert therefor --Table 4--.

Column 9, line 10, please delete "TABLE 3" and insert therefor --TABLE 4--.

Column 9, Table 3 Line 56 delete "CH" and insert therefor --$CH_3$- --.

Column 10, Line 36 delete "1H" and insert therefor --$^1H$--.

Column 10, Line 42 delete "(4,-bromophenyl)" and insert therefor --(4'-bromophenyl)--.

Column 10, Line 58 delete "(lit 136°-37°C.)" and insert therefor --(lit 136°-137°C.)--.

Column 10, Line 58 delete "$\delta$3430" and insert therefor --$\lambda$3430--.

Column 12, Line 40 delete "[$^{125}$]iodide" and insert therefor --[$^{125}$I]iodide--.

UNITED STATES PATENT AND TRADEMARK OFFICE
CERTIFICATE OF CORRECTION

PATENT NO. : 5,130,117
DATED : July 14, 1992
INVENTOR(S) : Hank F. Kung

It is certified that error appears in the above-identified patent and that said Letters Patent is hereby corrected as shown below:

Column 12, Line 46 delete "(3x1 mL." and insert therefor -- (3x1 mL).--.

Signed and Sealed this

Fourteenth Day of September, 1993

Attest:

BRUCE LEHMAN

Attesting Officer        Commissioner of Patents and Trademarks